(12) United States Patent
Crabb et al.

(10) Patent No.: US 6,174,294 B1
(45) Date of Patent: *Jan. 16, 2001

(54) LIMB LOAD MONITOR

(75) Inventors: Thomas M. Crabb, Middleton; Robert C. Richter, Cambridge; Anthony J. Kelhcut, Waukesha, all of WI (US)

(73) Assignee: Orbital Technologies, Inc., Madison, WI (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/691,740

(22) Filed: Aug. 2, 1996

Related U.S. Application Data

(60) Provisional application No. 60/001,879, filed on Aug. 3, 1995.

(51) Int. Cl.⁷ .................................................. A61B 5/103
(52) U.S. Cl. ............................................ 600/592; 600/595
(58) Field of Search ................................... 128/774, 782, 128/779

(56) References Cited

U.S. PATENT DOCUMENTS

| | | |
|---|---|---|
| 3,702,999 | 11/1972 | Gradisar . |
| 3,791,375 | 2/1974 | Pfeiffer . |
| 3,974,491 | 8/1976 | Sipe . |
| 4,387,472 * | 6/1983 | Wilson ................................. 128/779 |
| 4,647,918 | 3/1987 | Goforth . |
| 4,745,930 | 5/1988 | Confer . |
| 4,813,436 * | 3/1989 | Au ....................................... 128/779 |
| 5,107,854 | 4/1992 | Knotts et al. . |
| 5,253,654 | 10/1993 | Thomas et al. . |
| 5,437,289 * | 8/1995 | Liverance et al. .................... 128/779 |
| 5,505,072 * | 4/1996 | Oreper ....................................... 73/4 |
| 5,511,561 * | 4/1996 | Wanderman et al. ................ 128/779 |
| 5,619,186 * | 4/1997 | Schmidt et al. ...................... 340/573 |

* cited by examiner

*Primary Examiner*—Cary O'Connor
*Assistant Examiner*—Pamela Wingood

(57) ABSTRACT

A lower limb load monitor for providing feedback to a patient or user when a preselected force load is met or exceeded on a patient's or user's foot. The device includes one or more thin film force sensing elements positioned beneath the user's foot and connected with control means for providing a signal when a predetermined threshold force is met.

15 Claims, 4 Drawing Sheets

Fig. 1
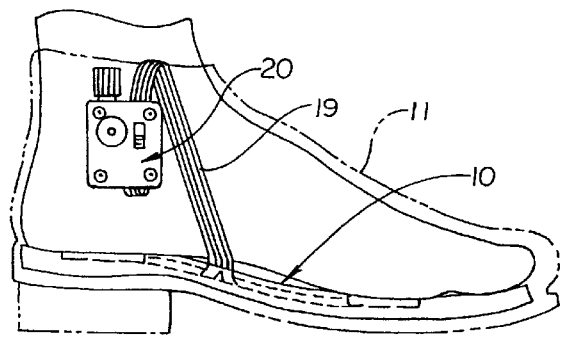
Fig. 2
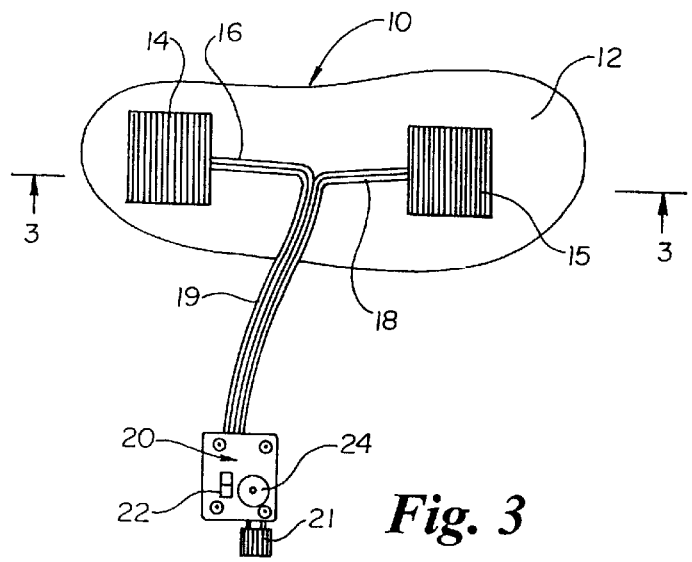
Fig. 3
Fig. 4
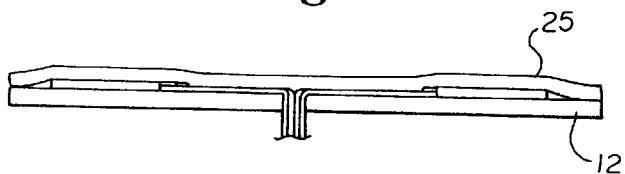

LIMB LOAD MONITOR

This application claims the benefit of U.S. Provisional Application No. 60/001,879 filed Aug. 3, 1995.

BACKGROUND OF THE INVENTION

1. Field of the Invention

The present invention relates generally to a limb load monitoring system, and more particularly to a lower limb load monitoring device for measuring or detecting the amount of force applied to, or weight borne by, a lower limb of the body (either natural or prosthetic) and providing a signal to the user when a predetermined threshold level is exceeded.

2. Description of the Prior Art

Numerous situations exist where it is important to limit the load or force which is applied to or borne by a lower natural or prosthetic limb of the body during standing, walking, stepping, running or jumping activities or during rehabilitation therapy. Situations also exist where it is important that the lower limb be exposed to a certain load or force, particularly during rehabilitation therapy. In both situations it is important to monitor such load or force and to provide a signal to the user when such force is exceeded or met. Examples include post-surgery or injury rehabilitation of hips, knees, ankles or any other portion of the body which is affected by force applied to or borne by at least one of the user's legs or any other situation in which monitoring of the weight on a lower limb during standing, walking, jumping or other activities is desired. Because of the clear economic benefits, including the potential of substituting outpatient care for clinical rehabilitation and the speeding or other enhancement of the rehabilitation process, the health care industry is exhibiting increased interest in improved devices which detect and monitor the force applied to the lower limbs.

Various patents currently exist which reflect the state of the art. One device is illustrated in U.S. Pat. No. 3,702,999 issued to Gradisar. In this device, a force sensitive means is positioned in two predetermined locations in the shoe of the user via a foot pad assembly: one beneath the heel and the other beneath the ball of the user's foot. Each of the force sensing means in this patent comprise a pair of electrical conductors which are spaced by a resilient dielectric member. Each of the force sensing means includes a set screw threadedly received by one of the conductors and extending toward the other. As a compressive force is applied to the pair of conductors, the resilient dielectric compresses causing the set screw to engage the other conductor. This closes the circuit and results in the generation of a signal. If the user desires the amount of force to be varied, the adjustment of the set screw is varied. Although this device conceptually provides a signalling device when a predetermined load is exceeded, the force sensing means themselves require a relatively thick profile since its operation requires vertical movement between two conductive plates with springloads between them. This creates a bulky orthopedic monitor which impedes the patient's normal walking style. Additionally, because of the mechanical nature of the pair of conductors, and the manner in which the set points are achieved, the patient, in some cases, must don and doff the device several times before achieving the correct calibrated set point. Also, variations in performance are inherent due to material wearing and aging. Still further, there is no means to combine the forces or loads of the two sensing means.

A second device is described in U.S. Pat. No. 4,745,930 issued to Confer. This device, however, is not a weight monitoring device, but instead is a force sensing insole used in association with an electro-goniometer for analyzing the gait of a patient. The device includes a multi-layer structure and a plurality of switches which sequentially close and open as the weight of the user is applied to the insole.

A further device described in U.S. Pat. No. 4,647,918 issued to Goforth relates a multi-event notification system for monitoring preselected critical pressure points on the feet of the user. This device discloses a plurality of battery powered pressure transducers in foot sensor pads for measuring the pressure at a number of points as a function of time. The information from such sensors is important for persons who have been diagnosed as having diminished sensation in the feet such as from diabetes mellitus. There is no disclosure in this patent of a device for warning the user of excessive instantaneous application of pressure or weight and accordingly it is not suitable for application as a lower limb load monitor.

Still other devices are described in U.S. Pat. No. 3,791,375 issued to Pfeiffer and U.S. Pat. No. 3,974,491 issued to Sipe. Although both relate generally to devices for signalling when excessive load is being borne by the lower limb, both devices rely on the detection of pressure created in a fluid containing load cell of the like. Thus, both are susceptible to failure from puncture to the fluid bladders. Further, contamination or degradation of the fluid can cause drift of sensor calibration or failure of the sensor in operation. Still further, the mechanical nature of the fluid transfer and the size of the tube required to transfer load information to a monitoring device necessarily requires a relatively bulky structure.

Accordingly, there is a need in the art for a lightweight, compact lower limb load monitor device which utilizes a relatively thin force sensing means for sensing both total load and load distribution.

SUMMARY OF THE INVENTION

In contrast to the prior art, the present invention relates to a lower limb load monitor which is lightweight, which does not suffer from mechanical wear because it has no mechanical or moving parts and in which all of the sensing components are sealed. Further, the force sensing element of the present invention is a "thin film" force sensor preferably on the order of less than 20–30 mils thick. Thus, the device does not significantly alter the walking style of the user. Further, the monitor of the preferred embodiment of the present invention is capable of monitoring total load on the lower limb as well as load distribution between various selected positions.

The force sensing element of the present invention utilizes a force measurement based on a change in electrical properties associated with the sensing element. Although it is contemplated that a variety of electrical properties may be utilized, the force sensor in accordance with the preferred embodiment embodies a pair of flat membranes in which a force variable circuitry is disposed between such membranes and in which the force applied to such membranes is measured as a function of the change in resistance in such circuitry.

The force sensing elements of the present invention may be positioned in an insole or an outsole embodiment and are electrically connected to an electronic control box positioned near the sensing elements. Preferably, the control box is sufficiently compact so that it can be attached to the user's belt or hip area, the shoe or other area surrounding the lower portion of the user's leg or foot. The control box includes source of a voltage or other electrical signal to the force sensing elements, a comparator to compare the resistivity or other electrical property of the force sensing elements to a set point, an alarm generator and an alarm or signalling means for providing a signal to the user when a predetermined force level is met or exceeded. The control box may also be provided with transmitting means for transmitting force information to a remote signalling device for providing a visual, audio, vibratory or some other signal at a remote location.

Accordingly, it is an object of the present invention to provide a lightweight, low cost lower limb load monitor.

Another object of the present invention is to provide a lower limb load monitor having heel and ball sensors and means for differentiating feedback signals from such sensors.

Another object of the present invention is to provide a lower limb load monitor utilizing flexible, thin film force sensing elements.

A further object of the present invention is to provide a lower limb load monitor having remote signalling means for signalling when a predetermined load is exceeded.

A still further object of the present invention is to provide a lower limb load monitor having a plurality of force sensing elements and control means for monitoring the total load of the sensor element or the load distribution at one or more selected elements.

Another object of the present invention is to provide a lower limb load monitor having a set point which is easily calibrated and maintained.

These and other objects of the present invention will become apparent with reference to the drawings, the description of the preferred embodiment and the appended claims.

DESCRIPTION OF THE DRAWINGS

FIG. 1 is a side elevational view showing a user's foot positioned on an insole embodiment of a limb load monitor in accordance with the present invention with the user's shoe illustrated in phantom.

FIG. 2 is an elevational plan view of the insole embodiment of the present invention.

FIG. 3 is a side view, partially in section as viewed along the section line 3—3 of FIG. 2, of the insole portion of insole embodiment of the present invention.

FIG. 4 is a side view similar to that of FIG. 3 of a modified insole embodiment in accordance with the present invention.

DESCRIPTION OF THE PREFERRED EMBODIMENT

Figure 5:
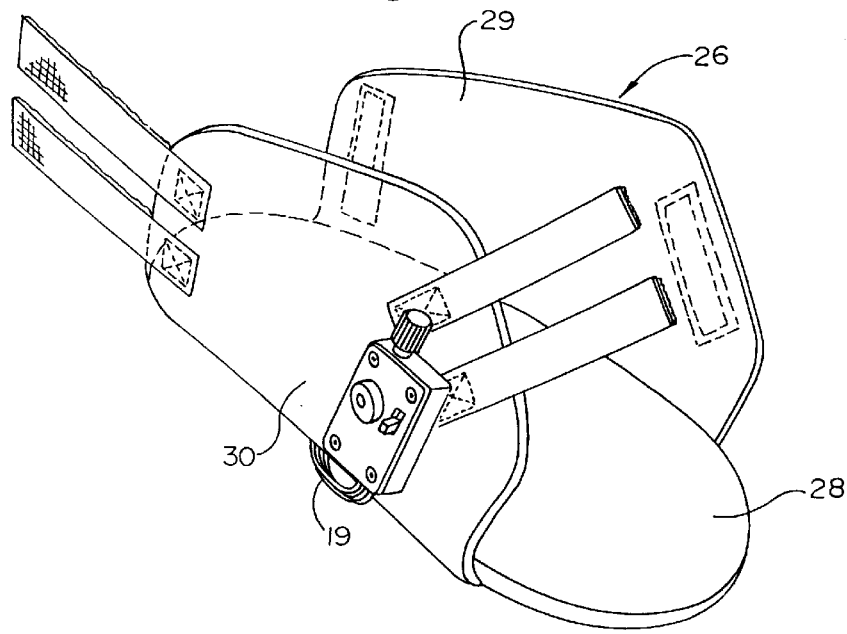
FIG. 5 is an isometric view of an outsole embodiment of the limb load monitor in accordance with the present invention.

Reference is first made to FIGS. 1, 2 and 3 illustrating an insole embodiment of the limb load monitor 10 in accordance with the present invention. FIG. 1 shows the monitor device 10 positioned within a user's shoe which is illustrated in phantom by the reference numeral 11. The insole embodiment of the present invention includes a substrate 12 having top and bottom surfaces in the shape of a conventional insole. As illustrated best in FIGS. 1 and 3, the substrate 12 is a relatively thin, single layer substrate which preferably is less than about 30 mils, and more preferably less than about 20 mils, thick. The substrate 12 may be constructed from a variety of materials, however, in the preferred embodiment the substrate 12 is constructed of a relatively hard plastic such as polystyrene. It is preferred that the material from which the substrate 12 is made be relatively flexible so that it can be easily inserted into the user's shoe and can flex, at least to some degree, during use, but which is hard enough to provide a relatively rigid, and noncompressible base for one or more force sensing elements.

In the preferred embodiments, a pair of force sensing elements 14 and 15 are secured to the top surface of the substrate 12 by adhesive means or the like and are positioned in the major or rehabilitatively important force bearing locations of the insole. More or less sensing elements could be provided for varying training and rehabilitation applications. The type of force sensors that are contemplated for use in accordance with the present invention are relatively thin and comprise a pair of sealed membranes with electrically conductive elements disposed between the membranes. These conductive elements function to exhibit a measurable electrical property in response to a compressive force relative to the major surfaces of the membrane. Thus, the sensing elements contemplated by the present invention are capable of sensing the magnitude of a force tending to compress the sensing element such as the weight of the user applied to the sensing elements in the device of the present invention. Preferably the sensing elements are less than 30 mils thick, more preferably less than about 20 mils and most preferably less than about 10 mils. Accordingly, force sensing elements of this type and of these thicknesses may be characterized as, and are referred in the present application as, "thin film" force sensors. Preferably, the sensing elements 14 and 15 are sensing elements which embody variable resistivity elements positioned between the membranes which exhibit a change in electrical resistance in response to the exertion of a force on such elements. However, it is contemplated that sensing elements may embody other electrical properties such as capacitance, inductance, and charge are also possible. These variable resistivity or other force sensors are relatively thin, flat sensors of the thickness described above. Sensors of the type used in the preferred embodiment are force sensing resistors sold by Interlink Electronics of Rockford, Calif.

As illustrated best in FIG. 2, the force sensing elements 14 and 15 are electrically connected to an electronic or control box 20. In the preferred embodiment, this electrical connection is provided by a four wire lead 19 which extends from the control box 20 and which is split into an electrical lead 16 comprising a pair of wires extending to the sensing element 14 and an electrical lead 18 comprising a pair of wires extending to the sensing element 15. The control box 20 includes, on its exterior, an on/off switch 22, a control knob 21 for varying the set point force level and an audio alarm 24. However, these elements may be positioned in other locations. The control box 20 may also include a switch or knob to control the level of output, a switch to choose monitoring of the force on the ball or heel of the foot or the summation of both, and a switch to enable differentiating or comparing feedback signals from sensors 14 and 15. The control knob 21 may also be provided with preselected calibrations.

A back surface of the control box 20, not shown in FIGS. 2 or 3, is provided with a layer of Velcro or a clip or other connection means for connection to the outside of the user's shoe as illustrated in FIG. 1 or to a garment or other mountable area or surface surrounding the user's body. In FIG. 1, the control box 20 is connected to the outer surface of the user's shoe, with the conductive lead 19 extending over the top of the user's shoe 11 for connection with the sensing elements 14 and 15. The control box may be connected to the inner surface of the user's shoe, and the lead may also extend a portion of the user's shoe or cast.

The embodiment of FIG. 4 is also an insole embodiment, similar to that of FIG. 3 except that FIG. 4 comprises a multiple layer substrate comprised of bottom or sole substrate portion 12 similar to in function and material to the substrate 12 of FIG. 3 as well as a top substrate portion 25 comprised of a thin, flexible synthetic material. Unlike the bottom substrate portion 20, the top substrate portion 25 is constructed of a relatively soft, resilient, flexible material. A principle function of the substrate layer 25 is to protect the sensor elements 14 and 15 and the conductive leads 16, 18 and 19 from being dislodged during use and to provide comfort to the user. The layer 25 may be connected with the layer 12 through any conventional means such as adhesive or the like. Preferably, the layer 25 is connected to the layer 12 in the multi-layer embodiment of FIG. 4 by a compliant adhesive, such as 3M 1099 plastic adhesive.

Figure 6:
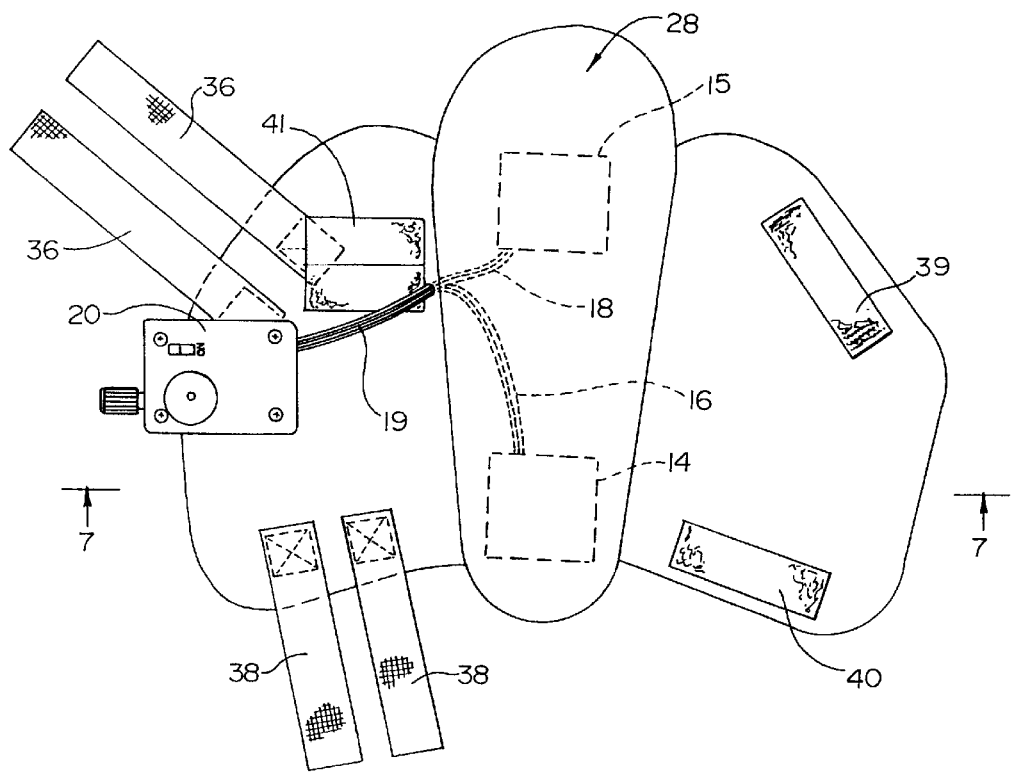
FIG. 6 is an elevational plan view of the outer side of the outsole embodiment of FIG. 5.
Figure 7:
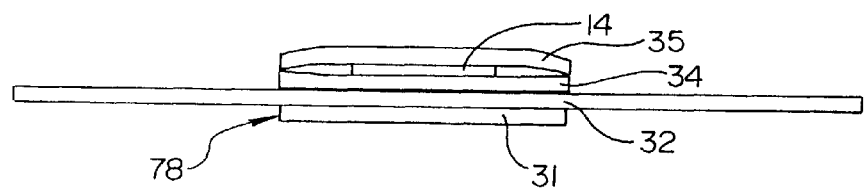
FIG. 7 is a view, partially in section, as viewed along the section line 7—7 of FIG. 6 and rotated 180°.

FIGS. 5, 6 and 7 illustrate a second or outsole embodiment of the present invention. With this embodiment, the device 26 is intended to be used outside of or over the user's normal shoe. In general, the device 26 includes a sole portion 28 having a shape similar to the sole of a conventional shoe and a pair of connection wings or sides 29 and 30 integrally formed with the sole portion 28 and extending outwardly from opposite sides to assist in connecting the device 26 to the user's shoe. As illustrated best in FIGS. 6 and 7, the sole portion 28 is a multi-layer element comprising a bottom layer 31, a first intermediate layer 32, a second intermediate layer 34 and a top layer 35.

In the preferred embodiment, the bottom layer 31 is comprised of a thin, relatively tough material such as a conventional shoe sole material. This layer 31 may have a variety of thicknesses, however, in the preferred embodiment, it is preferably about 20–60 mils thick. The first intermediate layer 32 is constructed of a thin, flexible material which extends outwardly beyond the edges of the sole portion 28 to form the connecting wings 29 and 30. In the preferred embodiment, the layer 32 is constructed of naugahyde or a vinyl-like material. The second intermediate layer 34 is a generally hard plastic material which is sufficiently flexible to accommodate at least some bending of the user's foot during use, but hard enough to form a good base for the force sensing elements 14 and 15. Preferably the layer 34 is about 10–20 mils thick and is preferably constructed of polyethylene plastic providing rigidity for sensor mounting, but flexibility for compliance with foot during movement.

The top layer 35 is constructed of a relatively thin and flexible material for padding the lower limb and is secured to the top surface of the layer 34 by an adhesive or the like. As best shown in FIG. 7, the top layer 35 and the layer 34 are secured together with the force sensing elements 14 and 15 positioned therebetween. Layers 31, 32 and 34 could be integrated into a single layer; however, layers 34 and 35 may be provided as a separate insole for integrated layers.

As shown best in FIG. 6, a pair of force sensing elements 14 and 15 are positioned relative to the sole portion 28 in positions similar to those of the insole embodiment of FIGS. 1–4, namely, at the heel and ball of the user's foot. Further, the sensing elements 14 and 15 are similar to those of the sensing elements 14 and 15 described above with respect to FIGS. 1–4. Also, similar to the embodiment of FIGS. 1–4, the electrical conductive leads 16, 18 and 19 connect the force sensing elements 14 and 15 to a control box 20 similar to that shown in FIGS. 1 and 2.

As shown best in FIGS. 5 and 6, the connecting wing 30 is integrally formed with, and extends outwardly from, a first side edge of the sole portion 28; but could also be integrated on the inside of the wing 30 with or without a protective cover with access to the control box 20 via an access hole. The wing 30 includes a first pair of connecting straps 36 extending forwardly from the forward end of the wing 30 and a second pair of connecting straps 38 extending rearwardly from the rearward end of the wing 30. The connecting wing 29 is integrally formed with, and extends outwardly from, a second side edge of the sole portion 28. The wing 29 includes connection strap portions 39 and 40 for connection with the straps 36 and 38, respectively. In the preferred embodiment, the connecting straps 36 and 38 are Velcro straps designed for connection to corresponding mating Velcro straps 39 and 40 on the side wing 29. The side wing 30 also includes a Velcro section 41 to which the control box 20 is connected.

Figure 9:
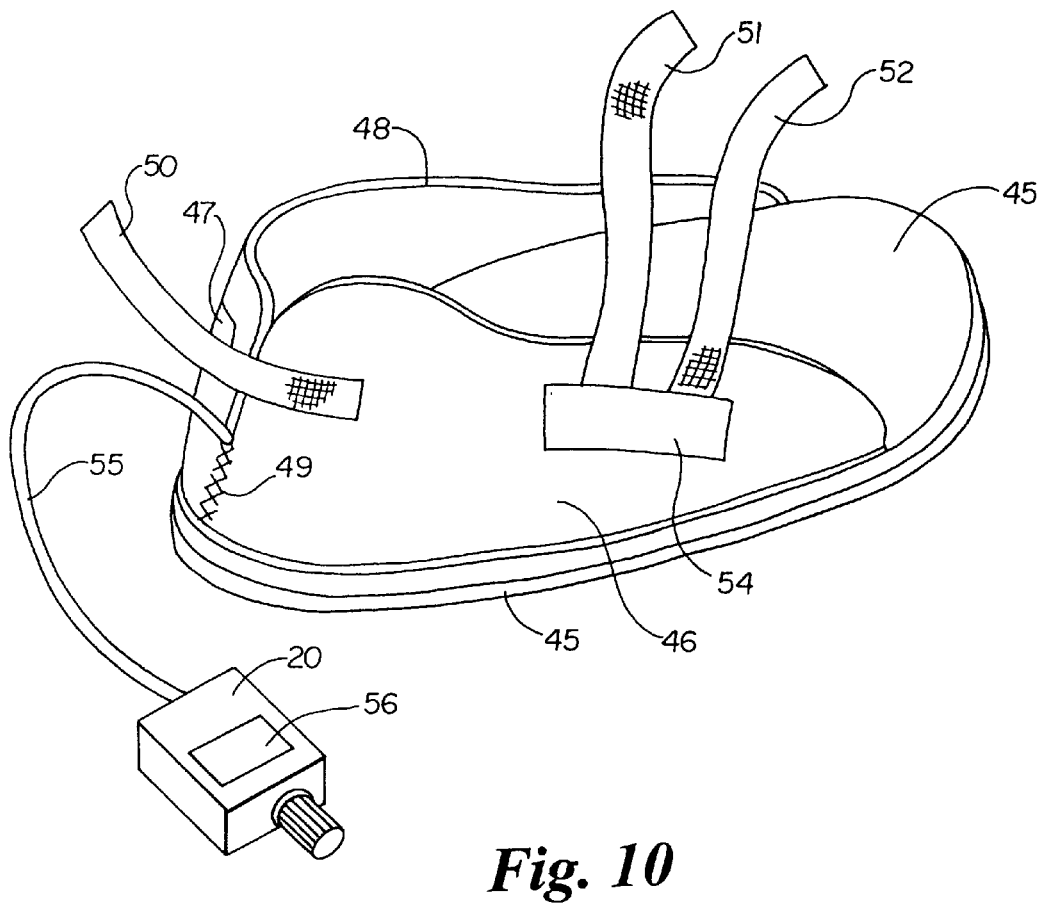
FIG. 9 is an isometric view of a further embodiment of an outsole boot incorporating the present invention.
Figure 10:
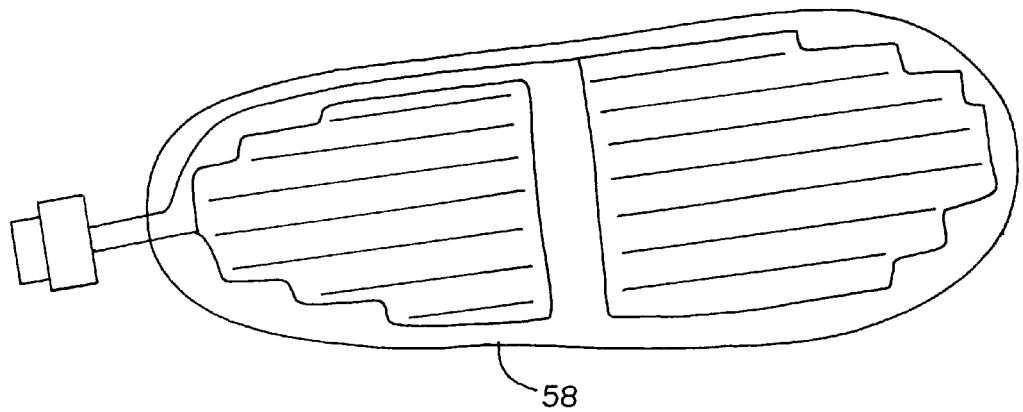
FIG. 10 is an elevational plan view of a modified force sensing element to be incorporated into either the insole or outsole embodiments.

FIG. 9 illustrates a further outsole embodiment. This embodiment includes a sole 45 and an upper portion comprised of a pair of side sections 46 and 48. The sections 46,48 are joined along their bottom edges to the outer side edges of the sole 45 by appropriate stitching. The lower rearward edge of each of the sections 46 and 48 connected by stitching 49. The upper rearward edges of the sections 46 and 48 are connectable by a Velcro strap 50 extending from the section 46 and a mating Velcro receiving portion 47 on the section 48. A pair of Velcro straps 51,52 extend from a forward portion of the section 46 for mating engagement with a Velcro receiving portion (not shown) on the section 48. A cord 55 extends from the rearward end of the boot and connects with a control box 20. The box 20 includes a Velcro patch 56. A Velcro base 54 is also provided on the section 46 to mate with the Velcro patch 56 and support the box 20, if desired. The embodiment of FIG. 9 may incorporate force sensors 14,15 such as those shown in FIGS. 2 and 6 or a force sensor 58 such as that shown in FIG. 10.

The embodiments of FIGS. 2 and 6 illustrate a pair of sensors 14 and 15. The sensor means can, however, be incorporated into a single element 58 such as that shown in FIG. 10. The element 58 may include single or multiple sensor components incorporated therein. All the sensors of the preferred and alternate embodiments are thin film force sensors as previously described.

Figure 8:
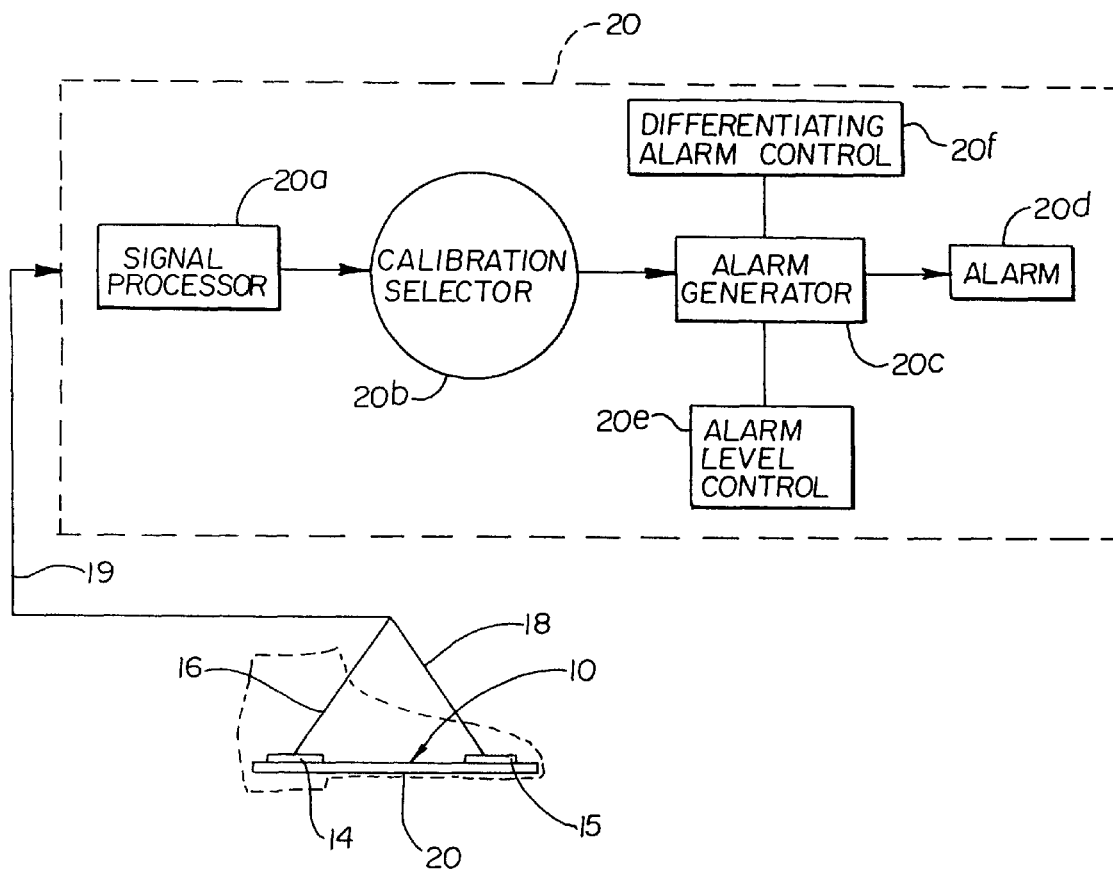
FIG. 8 is an electronic schematic diagram showing an insole embodiment in accordance with the present invention together with the functional electronic components of the control box.

Reference is next made to FIG. 8 illustrating the electronic functional elements within the control box 20. The control box 20, is battery powered and comprises a signal processor 20a, a calibration selector 20b, an alarm generator 20c, an alarm 20d, an alarm level control 20e, and a sensor selection and differentiation control 20f. Each of these components is produced utilizing integrated circuits, passive and/or active electrical components, and/or electromechanical devices there are commercially available. The interface between the sensor leads and the electronics occurs at the signal processor. The signal processor provides any necessary electrical power to the sensors 14 and 15 and in turn transforms the force sensitive electrical property of the sensors into an electrical signal. The purpose of the signal processor 20a is to filter electronic noise, should there be any, adjust the sensor signal range to the range needed for adjustment, and provide the proper output impedance for the succeeding electronic components. The calibration selector 20b provides the capability to adjust the weight level at which an output signal is generated. The alarm generator 20c is the output signal generator, which is controlled by the output of the calibration selector 20b. The alarm generator 20c in turn controls the alarm 20d. The alarm 20d may be in the form of a visual, audible or other sensory sensitive stimulations, or means of transmission of the data. The alarm is an electrically controlled device that is perceived by the human sensory system as an indicator that the preset weight level has been applied or exceeded. The level of the alarm may also be controlled by the element 20e. Further, different alarms may be provided for independent signalling of two sensors if desired.

The control box 20 may also be provided with a transmitter for remote signalling. In such case, the remote portion would be provided with a receiver and with the alarm components.

Although the description of the preferred embodiment has been quite specific, it is contemplated that various modifications could be made without deviating from the spirit of the present invention. Accordingly, it is intended that the scope of the present invention be dictated by the appended claims rather than by the description of the preferred embodiment.

We claim:

1. A fully portable device for sensing and providing feedback relative to the load on a lower limb of the user's body or on a prosthesis comprising:

a foot engagement device comprising one of an outsole for connection over the user's foot or other footwear or an insole for insertion within the user's footwear, said one outsole or insole including a substrate;

at least two separate and spaced film force sensing elements connected with said substrate, each of said sensing elements capable of providing a measurable electrical property having a level which varies as a function of the magnitude of a force applied to said sensing element, said substrate including a forward, ball portion and a rearward, heel portion and wherein at least two film force sensing elements includes a first force sensor positioned in the forward, ball portion of said substrate and a second film force sensor positioned in the rearward, heel portion of said substrate;

a control member connectable to a portion of the user's body at a location remote from said substrate and including a force sensor selector member to select said first force sensor, said second force sensor, or both, said control member including a signal processor operatively connected with said force sensing elements to compare the level of said measurable electrical property from said first force sensor, said second force sensor, or both to a preselected threshold level and an alarm signal generating member operatively connected with said signal processor to provide an alarm signal in response to the comparison status between the measurable electrical property from said first sensor, said second sensor, or both, and said preselected threshold level.

2. The device of claim 1 including electrical connection means between said force sensing elements and said signal processor.

3. The device of claim 1 including two or more thin film force sensing elements.

4. A device for sensing and providing feedback relative to the load on a lower limb of the body or on a prosthetic comprising:

a substrate;

two or more film force sensing elements connected with said substrate, each sensing element capable of providing a measurable electrical property having a level which varies as a function of the magnitude of a force applied to said sensor;

a signal processing means for comparing the level of said measurable electrical property of said sensing elements to a preselected threshold level and generating a signal in response to the comparison status between said measurable electrical property level and said preselected threshold level, wherein said signal processing means includes means for selectively comparing the individual level of said measurable electrical property from one of said force sensing elements to an individual preselected threshold level or the combined levels of said immeasurable electrical property from two or more of said force sensing elements to a combined preselected threshold level and said signal processing means further includes a selection switch for selectively comparing the individual level of said measurable electrical property from one of said force sensing elements to an individual preselected level or combined levels of said measurable electrical property from two or more of said force sensing elements to a combined preselected threshold level.

5. The device of claim 3 wherein said signal processing means includes means for selectively comparing the individual level of said measurable electrical property from one of said force sensing elements to an individual preselected threshold level.

6. The device of claim 1 wherein said measurable electrical property is resistance.

7. The device of claim 1 wherein thickness of said force sensing element is less than 30 mils.

8. The device of claim 1 wherein said control member includes an electrical power source.

9. The device of claim 8 wherein said sensing element includes a pair of electrical contacts.

10. The device of claim 2 wherein said electrical connection means provides a first voltage signal from said sensing element to said signal processor.

11. The device of claim 1 wherein said control member includes a threshold level control to preselect said preselected threshold level.

12. The device of claim 1 wherein said control member includes a threshold level selector member to pre-select a desired threshold force level.

13. The device of claim 1 wherein said signal process or is effective to compare said threshold force level to said selected first force sensor, said second force sensor, or both.

14. A limb load monitor for detecting the amount of force applied to a lower limb of the user's body and providing an alarm signal when a pre-determined threshold force level is exceeded, said limb load monitor comprising:

an outsole member comprising a substrate and connecting members for connecting said substrate to the users foot or foot wear, said substrate including a forward, ball portion and a rearward, heel portion;

a first film force sensor connected with said substrate in the forward portion of said substrate and a second film force sensor connected with said substrate in the rearward portion of said substrate, each of said first and second film force sensors being capable of providing a measurable electrical property having a level which varies as a function of the magnitude of a force applied to said sensor;

a control member connectable to a portion of the user's body remote from said substrate, said control member including a threshold level selector member to preselect a desired threshold force level, and a force sensor selector member to select said first force sensor, said second force sensor, or both;

separate electrical leads extending from said first force sensor and said second force sensor to said control member; and said control member including means to compare the combined level of measurable electrical property from said first and second sensors to said desired threshold level.

15. The limb load monitor of claim 14 wherein said control member includes a signal processor to compare said threshold force level to said selected first force sensor, said second force sensor, or both.

* * * * *